(12) United States Patent
Bitauld (10) Patent No.: US 10,928,894 B2
(45) Date of Patent: Feb. 23, 2021

(54) EYE TRACKING

(71) Applicant: Nokia Technologies Oy, Espoo (FI)

(72) Inventor: David Bitauld, Cambridge (GB)

(73) Assignee: Nokia Technologies Oy, Espoo (FI)

( * ) Notice: Subject to any disclaimer, the term of this patent is extended or adjusted under 35 U.S.C. 154(b) by 303 days.

(21) Appl. No.: 15/443,135

(22) Filed: Feb. 27, 2017

(65) Prior Publication Data

US 2018/0246566 A1   Aug. 30, 2018

(51) Int. Cl.

| | |
|---|---|
| *G02B 27/01* | (2006.01) |
| *G02B 27/00* | (2006.01) |
| *G02B 27/14* | (2006.01) |
| *G06F 3/01* | (2006.01) |

(52) U.S. Cl.
CPC ......... *G06F 3/013* (2013.01); *G02B 27/0093* (2013.01); *G02B 27/0172* (2013.01); *G02B 2027/014* (2013.01); *G02B 2027/0178* (2013.01)

(58) Field of Classification Search
None
See application file for complete search history.

(56) References Cited

U.S. PATENT DOCUMENTS

| | | | |
|---|---|---|---|
| 5,331,149 A | 7/1994 | Spitzer et al. | |
| 5,583,335 A | 12/1996 | Spitzer et al. | |
| 5,859,686 A | 1/1999 | Aboutalib et al. | |
| 6,433,760 B1 | 8/2002 | Vaissie et al. | |
| 6,560,028 B2 | 5/2003 | Melville et al. | |
| 6,758,563 B2 | 7/2004 | Levola | |
| 7,401,920 B1 | 7/2008 | Kranz et al. | |
| 8,878,749 B1* | 11/2014 | Wu | G01S 17/06 345/8 |
| 9,158,113 B2 | 10/2015 | Amirparviz et al. | |
| 9,261,959 B1* | 2/2016 | D'Amico | G06F 3/013 |
| 2004/0212712 A1 | 10/2004 | Stavely et al. | |
| 2009/0040461 A1* | 2/2009 | Efron | G02B 27/0093 351/210 |
| 2012/0075168 A1 | 3/2012 | Osterhout et al. | |
| 2013/0176533 A1 | 7/2013 | Raffle et al. | |
| 2015/0145777 A1 | 5/2015 | He et al. | |
| 2015/0277121 A1* | 10/2015 | Fridental | H04N 13/363 348/54 |
| 2015/0316982 A1 | 11/2015 | Miller | |
| 2016/0081547 A1* | 3/2016 | Gramatikov | G01N 21/23 351/210 |

(Continued)

OTHER PUBLICATIONS

Rigas et al., "Single-Pixel Eye Tracking via Patterned Contact Lenses: Design and Evaluation in HCI Domain", Proceedings of the 33rd Annual ACM Conference Extended Abstracts on Human Factors in Computing Systems, Apr. 18-23, 2015, pp. 1241-1246.

(Continued)

*Primary Examiner* — Kent W Chang
*Assistant Examiner* — Benjamin Morales
(74) *Attorney, Agent, or Firm* — Harrington & Smith (57) ABSTRACT

An apparatus including a display; a single pixel detector; and a beam splitter. The beam splitter is located relative to the display and the single pixel detector to allow a projected image from the display to pass through the beam splitter and direct a reflected image from an eye to the single pixel detector, where the reflected image is based at least partially upon the projected image.

18 Claims, 6 Drawing Sheets

(56) References Cited

U.S. PATENT DOCUMENTS

2016/0249801 A1 9/2016 Gao
2018/0239423 A1* 8/2018 Mardanbegi ............ A61B 3/113

OTHER PUBLICATIONS

Plopski et al., "Corneal Imaging Calibration for Optical See-Through Head-Mounted Displays" IEEE Transactions on Visualization and Computer Graphics, vol. 21, No. 4, Apr. 18, 2015, 10 Pages.
Hua et al., "A High-Resolution Optical See-Through Head-Mounted Display With Eyetracking Capability", Optic Express, vol. 21, No. 25, 2013, pp. 30993-30998.
Soldevila et al., "High-Resolution Adaptive Imaging With a Single Photodiode", Scientific Reports, Sep. 18, 2015, pp. 1-9.
"Here's How Google Glass Actually Works", Gizmodo, Retrieved on Apr. 27, 2017, Webpage available at : http://gizmodo.com/5994132/heres-how-google-glass-actually-works.
"Liquidmonitor Illus", Lightspeedca Design & Branding Group, Retrieved on Apr. 27, 2017, Webpage available at : http://www.lightspeedca.net/Liquidmonitor_illus.html.
"Natural Eye Optics (N.E.O.)", Immy, Retrieved on Apr. 27, 2017, Webpage available at : http://www.immyinc.com/.
Hua, "Sunglass-Like Displays Become a Reality With Free-Form Optical Technology", SPIE, Aug. 20, 2012, pp. 1-3.
Chinthammit et al., "A Shared-aperture Tracking Display for Augmented Reality", Massachusetts Institute of Technology, vol. 12, No. 1, Feb. 2003, pp. 1-18.
David et al., "Design of Integrated Eye Tracker-display Device for Head Mounted Systems", Proc. SPIE 7419, Infrared Systems and Photoelectronic Technology IV, vol. 7419, 2009, pp. 741910-1-741910-10.
Urey, "Diffractive Exit-Pupil Expander for Display Applications" Applied Optics, vol. 40, No. 32, Nov. 10, 2001, pp. 5840-5851.

* cited by examiner

EYE TRACKING

BACKGROUND

Technical Field

The exemplary and non-limiting embodiments relate generally to determining eye movement and/or gaze.

Brief Description of Prior Developments

Head mounted displays (HMD) are known. Eye tracking is known.

SUMMARY

The following summary is merely intended to be exemplary. The summary is not intended to limit the scope of the claims.

In accordance with one aspect, an example embodiment is provided in an apparatus comprising a display; a single pixel detector; and a beam splitter, where the beam splitter is located relative to the display and the single pixel detector to allow a projected image from the display to pass through the beam splitter and direct a reflected image from an eye to the single pixel detector, where the reflected image is based at least partially upon the projected image.

In accordance with another aspect, an example method comprises projecting a plurality of patterns from a display during projecting of a first image from the display, where the projecting of the plurality of patterns occurs at isolated instances during the projecting of the first image; and detecting reflected second images at a single pixel detector from an eye, where the reflected second images are based at least partially upon the plurality of patterns projected from the display.

In accordance with another aspect, an example embodiment is provided in an apparatus comprising at least one processor; and at least one non-transitory memory including computer program code, the at least one memory and the computer program code configured to, with the at least one processor, cause the apparatus to: project a plurality of patterns from a display during projecting of a first image from the display, where the projecting of the plurality of patterns occurs at isolated instances during the projecting of the first image; and determine an image of a portion of an eye based upon detecting reflected second images at a single pixel detector, where the reflected second images are based at least partially upon the plurality of patterns projected by the display during the projecting of the first image.

BRIEF DESCRIPTION OF THE DRAWINGS

The foregoing aspects and other features are explained in the following description, taken in connection with the accompanying drawings, wherein.

DETAILED DESCRIPTION OF EMBODIMENTS

Figure 1:
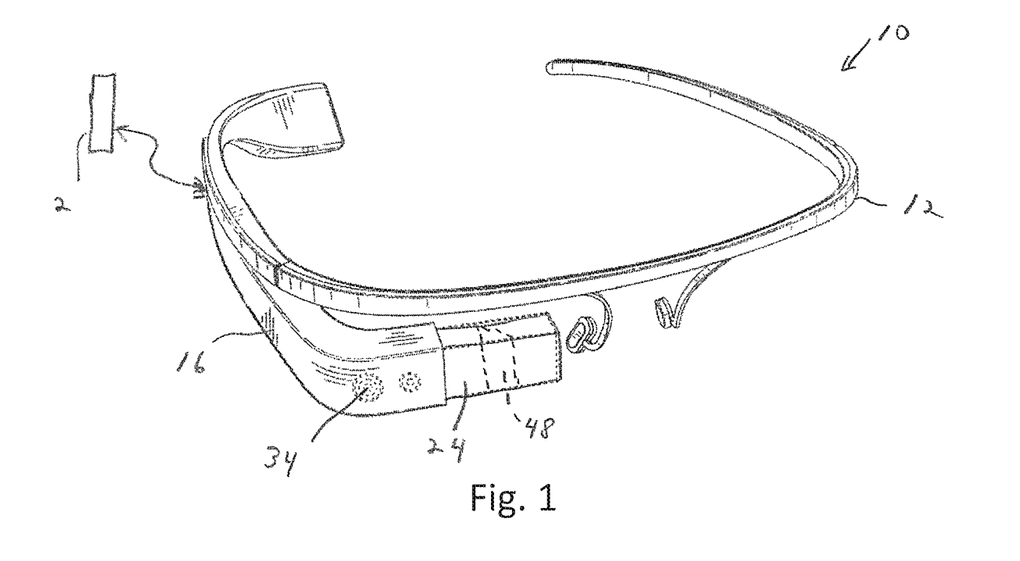
FIG. 1 is a perspective view of an example embodiment.

Referring to FIG. 1, there is shown a perspective view of an apparatus 10 incorporating features of an example embodiment. Although the features will be described with reference to the example embodiments shown in the drawings, it should be understood that features can be embodied in many alternate forms of embodiments. In addition, any suitable size, shape or type of elements or materials could be used.

Figure 2:
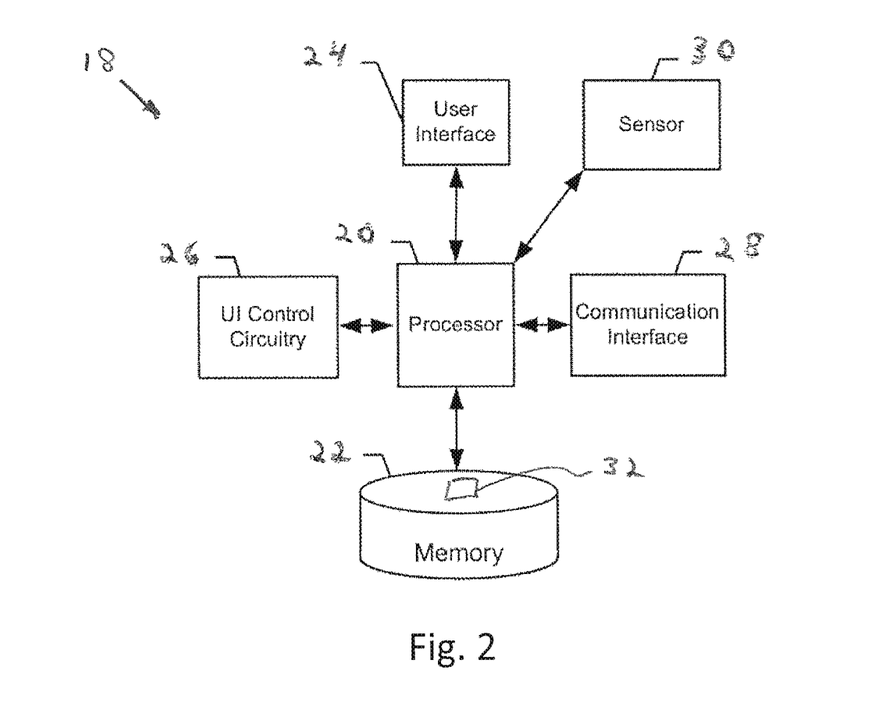
FIG. 2 is a diagram illustrating some of the components of the apparatus shown in FIG. 1.

The apparatus 10 in this example embodiment comprises a headset similar to eyeglasses for an augmented reality (AR) experience, such as similar to GOOGLE GLASS for example. The apparatus comprises a frame 12 and a section 16 for optical display and detection as further understood below. Referring also to FIG. 2, the section 16 includes circuitry 18 including, for example, a processor 20, a memory 22, a user interface (UI) 24, a user interface control circuitry 26, a wireless communication interface 28 and at least one sensor 30. The memory 22 may comprise software or code 32 for performing functions or operations as further described below. The wireless communication interface 28 may comprises a wireless transmitter and receiver, for example, to allow wireless communication to another device, such as device 2 shown in FIG. 1. The device 2 may be a smartphone, or a server, or a node for connection to the Internet for example. The device 2 may have a processor and memory including software for performing at least some of the operations described herein. The apparatus may also comprise other features, such as a camera 34 for example. A battery is also provided to power the section 16.

Figure 3:
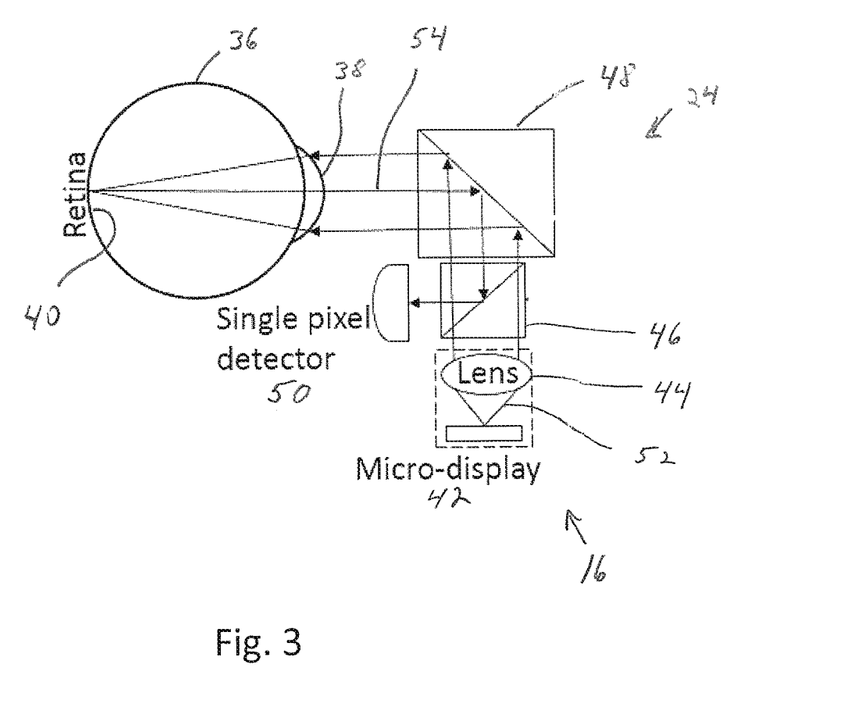
FIG. 3 is a diagram illustrating some of the components of the apparatus shown in FIG. 1.

Referring also to FIG. 3, a schematic diagram of an eye 36 of a user of the apparatus 10 is shown along with components of the section 16. The eye 36 includes a lens 38 and a retina 40. The user interface 24 includes a display 42, a lens 44, a beam splitter 46, a reflector 48 (provided as a second beam splitter in this example), and a detector 50 as at least one of the sensor(s) 30. In alternate example embodiments, additional or alternative components or arrangements of components may be provided. The display 42 in this example is a micro-display which is configured to project an image 52 as indicated by the lines from the display 42 to the lens 44. The projected image 52 may comprise, for example, a picture, a video, a software program interface, etc. The lens 44 focuses the image 52 into the direction through the beam splitter 46 and to the reflector 48 where the image is reflected to the eye 36 of the user. The lens 38 of the eye 36 focuses the projected image 52 on the retina 40. A reflected image 54 as indicated by the lines emanating off of the retina exits the eye 36 and is reflected by the see-through reflector 48 and the beam splitter 46 to the detector 50.

In the example shown, the detector 50 is a single pixel detector. Single pixel imaging benefits from fast improvement; both on the hardware side and the theory. For example, on the hardware side a Digital Micromirror Device (DMD), developed by Texas Instruments (TI), can project full high definition (HD) patterns at a rate of 20 kHz. On the theory side, compressive sensing has proven a very helpful tool for this type of imaging. Regular imaging with subsequent compression, on the other hand, requires a large amount of data to be collected from a sensor, while compressive sensing only collect the minimum amount of data required to reconstruct an image.

Figure 4:
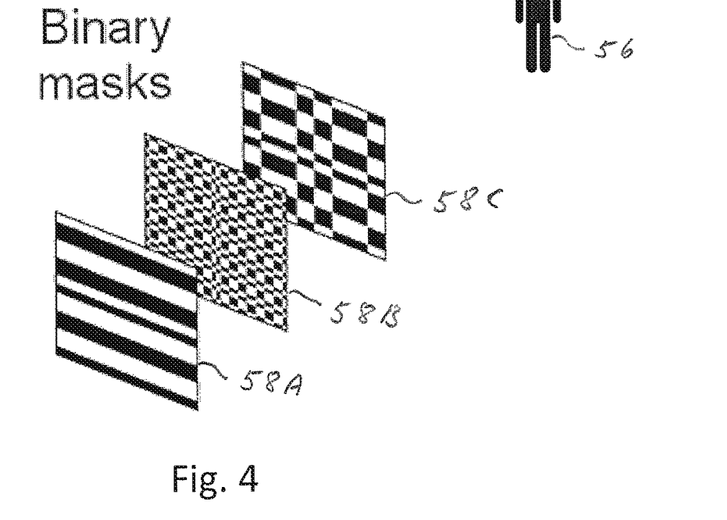
FIG. 4 is a diagram illustrating samples of projections from the display shown in FIG. 3.

In the case of single-pixel imaging, the collected data is a time series of single pixel intensities resulting from a wisely chosen sequence of illumination patterns. Thus, one way to produce an image of an object while using a single photodetector is to illuminate the object with a series of known patterns. Near eye displays (no matter which technology they use) project images on the human retina. Referring also to FIG. 4, with features as described herein, instead of merely projecting the image 56 of a scene by the display 42 onto the retina 40, the image 56 is combined with the above mentioned succession of patterns, 58A, 58B, 58C for example, and projected by the display 42 onto the retina 40 as the image 52. The reflected image 54 is then detected at the detector 50. With this reflected image 54, features as described herein may be used to obtain an image of the retina 40. This technique can easily be adapted to different types of micro-display-based HMD configurations. Once the image of the retina 40 is detected, the direction of gaze and/or eye tracking or eye movement may be determined.

Figure 5A:
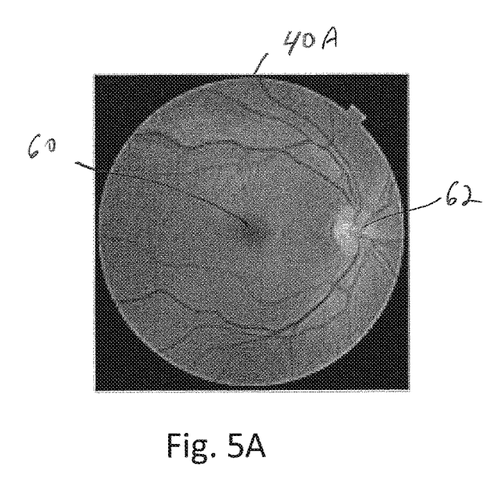
FIG. 5A is a picture illustrating a retinal image of a right eye.
Figure 5B:
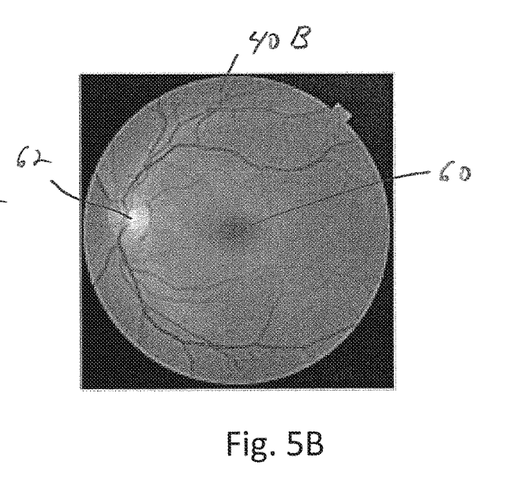
FIG. 5B is a picture illustrating a retinal image of a left eye.
Figure 5C:
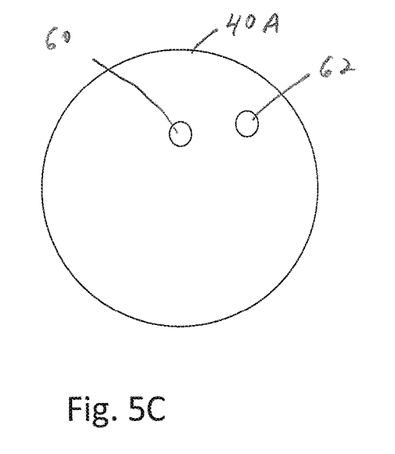
FIG. 5C is a schematic illustration of the retinal image of FIG. 5A with the eye looking up.
Figure 5D:
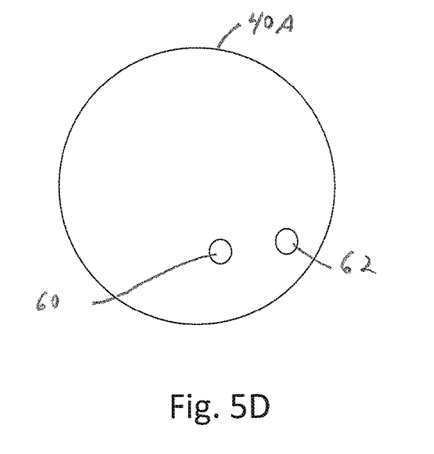
FIG. 5D is a schematic illustration of the retinal image of FIG. 5A with the eye looking down.

Referring also to FIGS. 5A and 5B, pictures of the retina 40A for a right eye and the retina 40B for a left eye are shown respectively. As can be seen, the macula 60 is generally in the center and the optic nerve or disc 62 is located relative to the macula as shown in the respective figures. For most people this type of structure (macula orientation relative to the optic nerve) is relatively the same. Thus, these types of structures as shown in FIGS. 5A and 5B are relatively easy to identify and are known. At low resolution, a dark spot (macula) indicates the center of the gaze and a bright spot (optic nerve) is located about 15 degree from the center (dark spot of the macula). Using a single pixel detection, the centroid of these features may be possible to calculate from a few tens of the patterns 58. For example, FIG. 5A shows the right eye looking straight, but FIG. 5C shows the right eye looking up and FIG. 5D shows the right eye looking down and slightly to the user's left.

Figure 6:
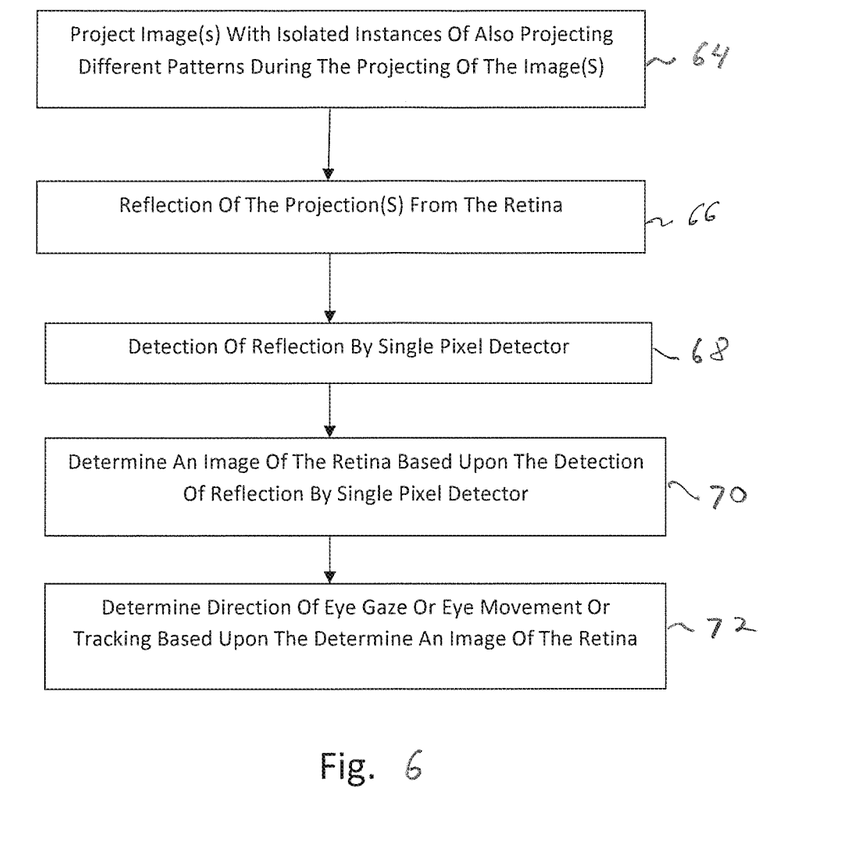
FIG. 6 is a diagram illustrating an example method.

Referring also to FIG. 6, features as described herein may be used with single-pixel eye tracking in a near-eye display; such as apparatus 10 for example. The image(s) 52 may be projected onto the retina 40 of the user with the system shown in FIG. 3 and, as indicated by block 64 in FIG. 6, isolated instances of projecting different patters 58 during the projecting of the image(s) 52 is also accomplished by the display 42. The processor 20 and the software 32 from the memory 22 may control the pattern 58 to be projected and the timing of the pattern projected relative to the projection of the image 56. As indicated by block 66, a reflected image 54 from the retina occurs caused by the images 52 (a combination of 56 and 58) hitting the retina 40. This reflected image 54 has image data regarding the retina 40 such as the X, Y coordinates of the macula 60 and optic nerve 62 relative to each other and relative to the overall image, such as illustrated by FIGS. 5A-5D for example. As indicated by block 68, the reflected image 54, such as illustrated by FIGS. 5A-5D for example, is detected by the single pixel detector 50. As illustrated by block 70 the processor 20 and software 32 may use the output from the single pixel detector 50 to determine, from a plurality of the reflected images 54, the image of the retina 40; where the plurality of reflected images are generated with respective different individual ones of the patterns 58. Using this determined image of the retina, the processor 20 and software 32 may determine a direction of eye gaze or eye movement or eye tracking as indicated by block 72. Alternatively, or additionally, the determined image of the retina may be output from the apparatus 10 by the communication interface 28 to another device, such as device 2 shown in FIG. 1 for example. Alternatively, or additionally, the output from the single pixel detector 50 may be output from the apparatus 10 by the communication interface 28 to another device, such as device 2 shown in FIG. 1 for example.

Eye tracking in Head Mounted Displays (HMD) may have many applications. For example, it may be used as a user interface to browse content in Virtual Reality (VR) or Augmented Reality (AR) environments, documents, internet, databases and others. By implementing eye tracking in a HMD, a user may be able to quickly navigate through a desired application(s), such as while performing another task (on a different device) for example. A user may, for example, browse and select with just an eye glance. It is also promising for specific needs of disabled users. It may also be used to adjust the focus/compression level/brightness of the projected image 52 depending on where the user is looking.

Eye tracking typically requires a camera which can take some space on a HMD, and adds cost to the HMD. Features as described herein may comprise use of a single pixel imaging technique for eye tracking instead of using a camera. An example embodiment may use an already existing image projector of a near-eye display with the addition of a single extra photodetector; to reconstruct an image of a retina 40 for example. The eye-tracking patterns 58 may be mixed with the images 56 in a way that projecting or superimposing of the patterns 58 is imperceptible by the user. Position of well-known retina features (such as, for example, the macula, optic nerve, and/or veins) may be used to determine the direction of the gaze. In the case of eye tracking by imaging the retina, not only are the reflected images 54 highly compressible, but also the reference image itself is known (FIGS. 5A and 5B for example). In one type of example embodiment the apparatus may be configured to record and store information about the retina of the actual user as a reference image in order to subsequently recognize the reflected image during later use. For eye tracking, the only data needed is an X,Y value for the keying features (such as macula and optic nerve for example) by which the reflected image is determined to have shifted or moved.

As an example of where the single-pixel detector can be located, FIG. 3 represents merely one example location of the detector and beam splitter, and should not be considered as limiting. The reflected image 54 coming back from the retina 40 may be extracted anywhere between the eye 36 and the display 42. The extraction is made by a beam splitter in this example because the reflected image 54 follows the same path as the projected image 52.

Figures 7A, 7B:
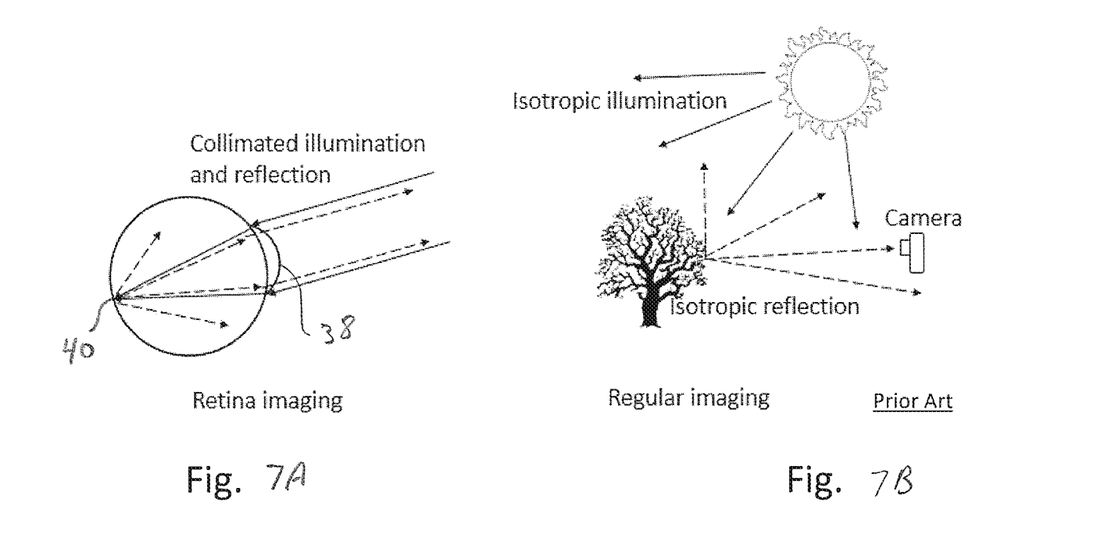
FIG. 7A is a diagram illustrating a collimated illumination and reflection at an eye.
FIG. 7B is a diagram illustrating a conventional imaging with a camera.

For the augmented reality (AR) example shown in FIG. 3, the photodetector 50 may collect as much light as possible from the retina 40 without blocking the vision of the user. The reflectivity of the beam splitter 48 may, therefore, be adjusted to get the best trade-off. However, apart from this trade-off, the collection of the reflected image 54 is very efficient because it is collimated by the lens 38 of the eye 36. As illustrated by FIG. 7A, on one hand, the illumination of the retina 40 is optimal by design because illumination of the retina 40 is the original purpose of the head mounted display and, on the other hand, the collection of the light is facilitated by the eye lens 38, which makes the imaging process optimal. The collection of light in this system is even more efficient than regular imaging in a camera shown for example in FIG. 7B. In regular imaging, as shown in FIG. 7B, a very small fraction of the light is collected by the aperture of a camera. However, features as described herein benefit from the fact that, by design, the illumination and reflection are collimated. Collimated light is light whose rays are parallel and, therefore, will spread minimally as it propagates. A perfectly collimated beam, with no divergence, would not disperse with distance.

A proportion of the light diffused by the retina will not find its way out of the eye, but all the light coming out of the pupil will contra-propagate back towards the display 42. Therefore, by placing the beam splitter 46 in front of the display 42, and using the single single-pixel detector having a similar area as the display 42, all the light out of the eye, as the reflected image, may be collected. This advantage compensates for the fact that the beam splitter reflection and pattern coefficient (e) may be small enough to keep a good display luminosity. Once the system has determined an image of the retina from the multiple outputs from the single pixel detector 50, it is easy to calculate where the user is looking by measuring the positions of the macula (dark region), the optic nerve (bright region) and/or the veins through adapted image recognition.

Figure 8A:
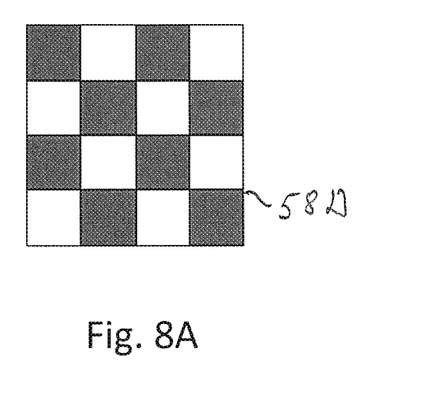
FIGS. 8A and 8B illustrate portions of complementary pairs of patters shown in FIG. 4.
Figure 8B:
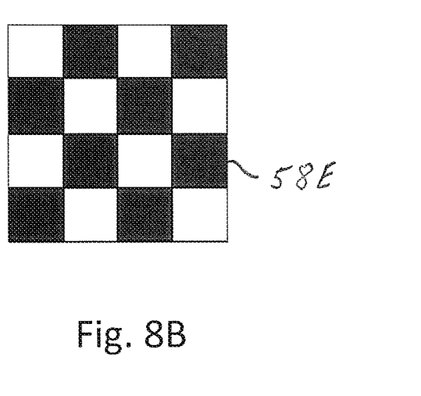

In order to make the measurement of the retina image via the added patterns 58 invisible to the user, it is possible to superimpose the patterns 58 to the projected image or scene 56 and change the patterns 58 faster that the user (having the eye 36) can perceive. These patterns 58 may be used as a slight modification on the projected image 56 such as, for example:

I(x,y): the image 56 changes at 25 fps;
P(x,y): the patterns 58 changing at 20,000 fps; and
thus, the projected image 52 allowing simultaneously to project the image and track the eye would be:

$$I(x,y)*(1+\varepsilon P(x,y))$$

with ε being a small number. In one type of example, the patterns 58 may be provided as complementary pairs to ensure that the average is invisible. For example, compare the portion of the pattern 58D shown in FIG. 8A to the same portion of the pattern 58E shown in FIG. 8B. Rather than superimposing the patters 58, the patterns may be switched in and out relative to the image(s) 56.

Speed

Single pixel imaging techniques are constantly improving. With currently available technologies the direction of a gaze may be retrieved in a very short time. This is because, for example:

the pattern frame rate is fast (such as 20 kHz for example); and
the required number of patterns is small because, for example:
the reflected image 54 is highly compressible, and
the image features of the retina 40 are known.

Assuming a few tens of projections using the different patterns 58 are enough, the gaze direction may be retrieved in a few milliseconds. This is faster than the eye can move. Thus, there is little issue in regard to an eye 36 moving between two patterns.

Field of View

Displays are, by definition, designed to illuminate the center of the retina and the reflected light automatically comes back in the exact opposite direction. This means that, as long as the user is looking at the display, the relevant parts of the retina may be imaged. If the user is looking at the edges of a displayed image, although it is possible that the optic nerve, which is about 12 degree from the center, might not be visible, the macula should still be visible.

Amount of Light Collected

This example configuration may be used to efficiently collect light from the retina. This type of collection is even better that normal imaging, such as with a camera as shown in FIG. 7B for example. This may sound counterintuitive because a person ordinarily does not manage to see other people's retina in everyday life. However, with features as described herein, the examples are not illuminating and collecting the light from the same direction. The illuminating is in one direction and the collection is, at least partially, in a different direction. The only everyday example where this type of condition is seen is the "red eye" effect on pictures with flash. Then the retina is visible during flash photography, the "red eye" effect is seen as bright red spots in the eyes.

Contrast

With features as described herein, the contrast will not reduce. Only the luminosity will reduce by a few percents depending on the chosen trade-offs. This should not be perceptible to the user. As the equation above shows, the image intensity is modulated, but black remains black. This might be a problem if the user is looking at something completely black. However, in one example embodiment, if the user is looking at a black area, but images are still present around the black area, image recognition of the veins in non-central areas of the eye may be used. In one type of example, if the whole display is black and eye tracking is needed at the same time (which may be rare) the contrast may be decreased and a very dark grey may appear instead of black. If this is a problem, another example may comprise use of non-visible wavelengths for pattern projection. Infrared may not see the macula, but infrared light may give a very good image of the veins and the optic nerve. Although ultraviolet light may be used to see the macula, ultraviolet light does not transmit very well through the cornea. In one type of example, multiple types of light could be used.

An advantage of a system as described above is provision of eye-tracking, but with very little extra hardware compared to conventional head mounted displays. The processor may use fast image processing to accomplish this eye-tracking using one or more single pixel detectors.

Figure 9:
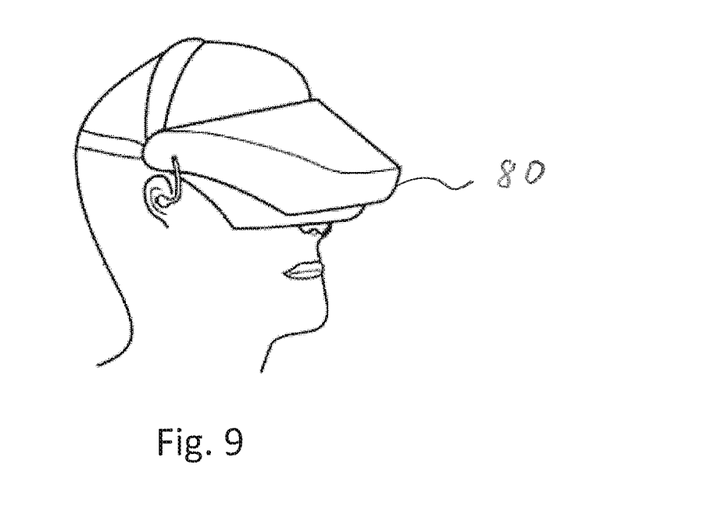
FIG. 9 illustrates an example of a virtual reality headset which may have features as described herein.
Figure 10:
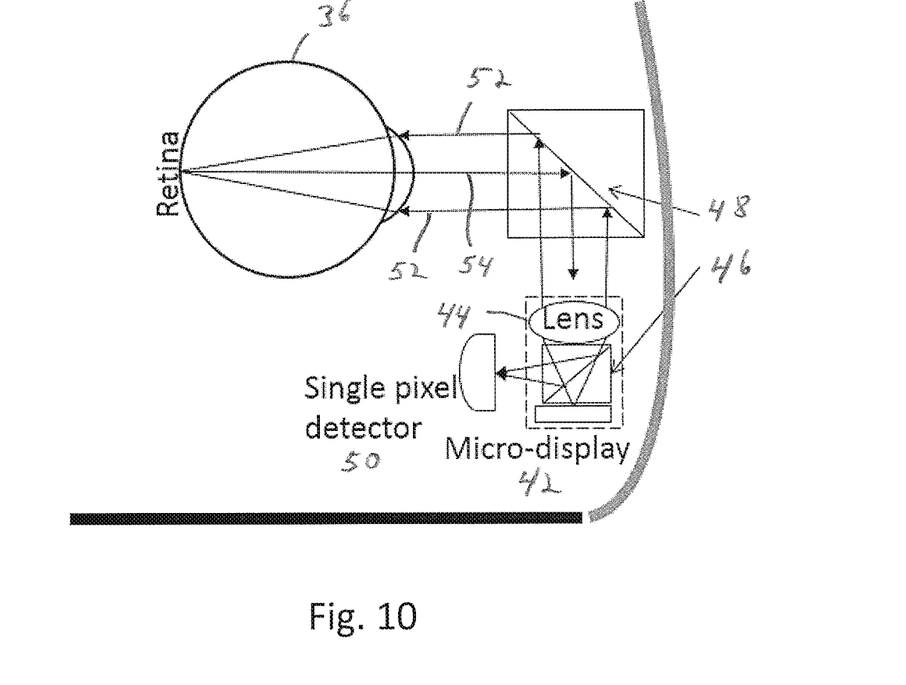
FIG. 10 is a diagram similar to FIG. 3 showing another example embodiment.

Referring also to FIG. 9, another example is shown. In this example the head mounted display (HMD) 80 comprises a virtual reality (VR) headset. This example helps to illustrate that features as described herein are not limited to an AR headset. Referring also to FIG. 10, another example is shown similar to FIG. 3. In this example the beam splitter 46 is located between the display 42 and the lens 44.

An example embodiment may be provided in an apparatus comprising a display; a single pixel detector; and a beam splitter, where the beam splitter is located relative to the display and the single pixel detector to allow a projected image from the display to pass through the beam splitter and direct a reflected image from an eye to the single pixel detector, where the reflected image is based at least partially upon the projected image.

The apparatus may be configured to display the projected image from the display as comprising at least one first image and a plurality of patterns during the projecting of the at least one first image, where the projecting of the plurality of patterns occurs at isolated instances during the projecting of the at least one first image. The apparatus may be configured to superimpose the plurality of patterns on the first images. The apparatus may comprise a head mounted display (HMD). The head mounted display (HMD) may comprise a see-through reflector located relative to the beam splitter to reflect the image from the beam splitter towards the eye and reflect an image from the eye to the beam splitter as the reflected image. The apparatus may further comprise a controller connected to the single pixel detector, where the controller is configured to determine an image of a retina of the eye based upon a plurality of the reflected images detected at the single pixel detector, where the reflected images are based at least partially upon patterns projected by the display. The apparatus may further comprise a controller connected to the display, where the controller is configured to separately superimpose different patterns with content projected by the display, where the projecting of each of the respective ones of the patterns occurs at respective individual instances during the projecting of the content by the display. The patterns may comprise binary masks.

An example method may comprise projecting a plurality of patterns from a display during projecting of a first image from the display, where the projecting of the plurality of patterns occurs at isolated instances during the projecting of the first image; and detecting reflected second images at a single pixel detector from an eye, where the reflected second images are based at least partially upon the plurality of patterns projected from the display. The first image may comprise content projected by the display, and where each of the plurality of patterns are separately superimposed with the content projected by the display. The first image and the plurality of patterns from the display may be reflected at a see-through reflector towards the eye, and where images of the eye are reflected at the see-through reflector as the reflected second images. The patterns may comprise binary masks. Projecting the plurality of patterns may comprise sequentially projecting complementary pairs of the patterns at a timing such that the patterns are not perceptible by a user. The method may further comprise determining an image of a retina of the eye based upon a plurality of the reflected second images detected at the single pixel detector, where the reflected second images are based at least partially upon the plurality of patterns projected by the display. The method may further comprise tracking movement of the eye based upon the determined reflected second images of the eye. A non-transitory program storage device readable by a machine, tangibly embodying a program of instructions executable by the machine for performing operations, may be provided, such as memory 22 for example, comprising the method operations or steps described above.

An embodiment may be provided in an apparatus comprising at least one processor; and at least one non-transitory memory including computer program code, the at least one memory and the computer program code configured to, with the at least one processor, cause the apparatus to: project a plurality of patterns from a display during projecting of a first image from the display, where the projecting of the plurality of patterns occurs at isolated instances during the projecting of the first image; and determine an image of a portion of an eye based upon detecting reflected second images at a single pixel detector, where the reflected second images are based at least partially upon the plurality of patterns projected by the display during the projecting of the first image.

The apparatus may comprise a beam splitter located relative to the display and the single pixel detector to allow the first image and the plurality of patterns from the display to pass through the beam splitter and direct the reflected second images from the eye to the single pixel detector. The at least one memory and the computer program code may be configured to, with the at least one processor, cause the apparatus to separately superimpose different ones of the patterns with the first image projected by the display. The at least one memory and the computer program code may be configured to, with the at least one processor, cause the apparatus to track movement of the eye based upon the determined image of the portion of the eye.

An example apparatus may be provided comprising means for projecting a plurality of patterns from a display during projecting of a first image from the display, where the projecting of the plurality of patterns occurs at isolated instances during the projecting of the first image; and means for detecting reflected second images at a single pixel detector from an eye, where the reflected second images are based at least partially upon the plurality of patterns projected from the display. The apparatus may comprise means for determining an image of a portion of the eye, such as a retina for example, and means for determining or tracking eye movement and/or gaze based upon the determined image of the portion of the eye.

Any combination of one or more computer readable medium(s) may be utilized as the memory. The computer readable medium may be a computer readable signal medium or a non-transitory computer readable storage medium. A non-transitory computer readable storage medium does not include propagating signals and may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing.

It should be understood that the foregoing description is only illustrative. Various alternatives and modifications can be devised by those skilled in the art. For example, features recited in the various dependent claims could be combined with each other in any suitable combination(s). In addition, features from different embodiments described above could be selectively combined into a new embodiment. Accordingly, the description is intended to embrace all such alternatives, modifications and variances which fall within the scope of the appended claims.

What is claimed is:

1. An apparatus comprising:
a display for projecting a plurality of images toward an eye of a user, said plurality of image including at least one fixed pattern;
a reflector, said reflector reflecting said plurality of images from the display toward the eye of the user, said reflector further reflecting a plurality of reflected images from a retina of the eye of the user back toward the display, said plurality of reflected images including at least one reflected fixed pattern;

a beam splitter, said beam splitter being disposed between said reflector and said display;

a single pixel detector, said single pixel detector being disposed to detect the plurality of reflected images reflected by the retina of the eye of the user, by the reflector, and by the beam splitter; and a controller, said controller determining an image of the retina from the at least one reflected fixed pattern in said plurality of reflected images detected by the single pixel detector, said controller further tracking movement of the eye based on differences between successive images of the retina.

2. The apparatus as claimed in claim 1, wherein the apparatus is configured to project the projected image from the display as comprising at least one first image and a plurality of patterns, where the projection of the plurality of patterns occurs at respective instances during the projection of the at least one first image.

3. The apparatus as claimed in claim 2, wherein the apparatus is configured to superimpose the plurality of patterns on the at least one first image.

4. The apparatus as claimed in claim 1, wherein whom the apparatus comprises a head-mounted display (HMD).

5. The apparatus as claimed in claim 4, wherein the head-mounted display (HMD) comprises a see-through reflector located relative to the beam splitter to reflect the projected image from the beam splitter towards the eye and reflect the reflected image from the eye to the beam splitter.

6. The apparatus as claimed in claim 1, further comprising;

a controller connected to the display, where the controller is configured to separately superimpose different patterns with content projected by the display, where the projecting of each of the respective ones of the patterns occurs at isolated instances during the projecting of the content by the display.

7. The apparatus as claimed in claim 1, wherein the single-pixel detector comprises a sole single-pixel detector in the apparatus.

8. A method comprising:

projecting a plurality of images from a display toward an eye of a user, said plurality of images including at least one fixed pattern;

reflecting said plurality of images toward the eye of the user;

reflecting a plurality of reflected images from a retina of the eye of the user back toward the display, said plurality of reflected images including at least one reflected fixed pattern;

detecting said plurality of reflected images reflected by the retina of the eye of the user, said plurality of reflected images including sat least one reflected fixed pattern;

determining an image of the retina from the at least one reflected fixed pattern in said plurality of reflected images; and tracking movement of the eye based on differences between successive images of the retina.

9. The method as claimed in claim 8, wherein the plurality of images includes at least one first image comprising content projected by the display, and wherein the at least one fixed pattern is separately superimposed with the content projected by the display.

10. The method as claimed in claim 8, wherein the plurality of images includes at least one first image comprising content projected by the display and the at least one fixed pattern from the display is reflected at a see-through reflector towards the eye, and wherein reflected second images of the eye are reflected at the see-through reflector.

11. The method as claimed in claim 8, wherein the at least one fixed pattern comprises a binary mask.

12. The method as claimed in claim 8, wherein projecting the plurality of images comprises sequentially projecting complementary pairs of the fixed patterns at a timing such that the fixed patterns are not perceptible by the user.

13. The method as claimed in claim 8, wherein determining an image of the retina from the at least one reflected fixed pattern in said plurality of reflected images is based upon a plurality of reflected second images detected at a single pixel detector, wherein the reflected second images are based at least partially upon the at least one fixed pattern projected by the display.

14. A non-transitory program storage device readable by a machine, tangibly embodying a program of instructions executable by the machine for performing operations, the operations comprising the method as claimed in claim 8.

15. An apparatus comprising:

at least one processor, and at least one non-transitory memory including computer program code, the at least one memory and the computer program code configured, with the at least one processor, to cause the apparatus to:

project a plurality of images from a display toward an eye of a user, said plurality of images including at least one fixed pattern;

reflect said plurality of images toward the eye of the user;

reflect a plurality of reflected images from a retina of the eye of the user back toward the display, said plurality of reflected images including at least one reflected fixed pattern;

detect said plurality of reflected images reflected by the retina of the eye of the user, said plurality of reflected images including aid at least one reflected fixed pattern;

determine an image of the retina from the at least one reflected fixed pattern in said plurality of reflected images; and track movement of the eye based on differences between successive images of the retina.

16. The apparatus as claimed in claim 15, wherein the apparatus further comprises a beam splitter located relative to the display and a single-pixel detector to allow the plurality of images including at least one fixed pattern from the display to pass through the beam splitter and to direct reflected second images from the eye to the single-pixel detector.

17. The apparatus as claimed in claim 15, wherein the at least one memory and the computer program code are configured, with the at least one processor, to cause the apparatus to separately superimpose different ones of the at least one fixed pattern with the plurality of images projected by the display.

18. The apparatus as claimed in claim 15, wherein the at least one memory and the computer program code are configured, with the at least one processor, to cause the apparatus to track movement of the eye based upon the determined image of the retina of the eye.

* * * * *